United States Patent [19]

Glick et al.

[11] 4,008,303

[45] Feb. 15, 1977

[54] PROCESS FOR EXTRUDING GREEN POLYGLYCOLIC ACID SUTURES AND SURGICAL ELEMENTS

[75] Inventors: Arthur Glick, Danbury; Lester Daniel Chirgwin, Jr., Stamford, both of Conn.

[73] Assignee: American Cyanamid Company, Stamford, Conn.

[22] Filed: Aug. 3, 1972

[21] Appl. No.: 277,537

Related U.S. Application Data

[63] Continuation-in-part of Ser. No. 176,291, Aug. 30, 1971, abandoned.

[52] U.S. Cl. .................. 264/210 F; 128/335.5; 264/211
[51] Int. Cl.² ............................................. D01D 5/12
[58] Field of Search .......... 260/40 P, 37 P, 78.3 R; 264/78, 210 F, 211; 128/335.5

[56] References Cited

UNITED STATES PATENTS

| | | | |
|---|---|---|---|
| 2,909,177 | 10/1959 | Dowd et al. | 128/335.5 |
| 3,297,033 | 1/1967 | Schmitt et al. | 128/335.5 |
| 3,487,041 | 12/1969 | Okuzumi | 260/40 R |
| 3,636,956 | 1/1972 | Schneider | 260/78.3 |

FOREIGN PATENTS OR APPLICATIONS 988,939   4/1965   United Kingdom ................. 264/78

*Primary Examiner*—Jay H. Woo
*Attorney, Agent, or Firm*—Samuel Branch Walker

[57] ABSTRACT

Polyglycolic acid surgical elements, particularly sutures, are colored green to contrast with tissue, blood, and surroundings by extruding while melted the polyglycolic acid and concurrently in an optically homogeneous dispersion, from about 0.03% to 0.5% by weight of 1,4-bis(p-toluidino)-anthraquinone (D&C Green No. 6).

9 Claims, No Drawings

PROCESS FOR EXTRUDING GREEN POLYGLYCOLIC ACID SUTURES AND SURGICAL ELEMENTS

CROSS-REFERENCE TO RELATED APPLICATIONS

This application is a continuation-in-part of our application Ser. No. 176,291 filed Aug. 30, 1971, now abandoned.

BACKGROUND OF THE INVENTION

Absorbable surgical sutures of polyglycolic acid have recently been made available to surgeons.

As set forth in U.S. Pat. No. 3,297,033, polyhydroxyacetic ester is sometimes referred to as polyglycolide, or poly(glycolic acid) and can be considered as essentially a product of polymerization of glycolic acid, that is, hydroxyacetic acid, which in simplified form is shown by the equation:

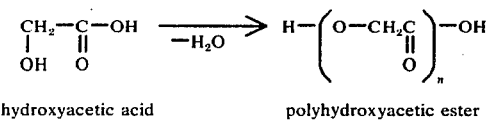

hydroxyacetic acid      polyhydroxyacetic ester

For use as a suture, preferably $n$ is such that the molecular weight is in the range of 10,000 or more. Above 100,000 the polymer is difficult to extrude.

In these molecular weight ranges the polymer has a melt viscosity at 245° C. of between about 400 and about 27,000 poises. Because the fiber is from a synthetic and controllable source, with a controlled molecular weight and controlled small percentage of comonomer, the absorbability, stiffness and other characteristics can be modified. In general, the higher the molecular weight, the slower the rate of absorption under a given set of conditions.

Among several methods by which polyhydroxyacetic ester can be prepared, one preferred route involves the polymerization of glycolide,

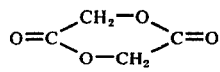

the cyclic dimeric condensation product formed by dehydrating hydroxyacetic acid. During polymerization of glycolide, the ring is broken and straight-chain polymerization occurs. Probably at least a small portion of the polymerization involves the formation of anhydride or ether linkages from a condensation of glycolic acid in a head-to-head, or tail-to-tail direction. The current state of the art is not sufficiently advanced to show with certainty the ratio of anhydride or ether linkages to ester group but indicates there are no more than a few percent of the total. A small quantity of methoxyacetic acid,

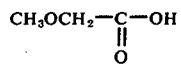

or methyl hydroxyacetic ester,

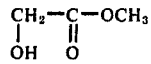

or their homologs, such as higher alkoxyacetic acids, or alkyl hydroxyacetic esters may be present during the polymerization as an end group stabilizer controlling the molecular weight and viscosity. Small quantities of other materials may be present in the chain, as for example d,l-lactic acid, its optically active forms, homologs, and analogs.

Said U.S. Pat. No. 3,297,033 incorporates a reference to U.S. Pat. No. 2,668,162 — Lowe which quantifies a small amount of lactides as up to 15%, disclosing for example the preparation of a copolymer of 90/10 glycolide/lactide offers two advantages over the homopolymer of glycolide. One advantage is that the melting point of the copolymer is lower than the homopolymer, being in the neighborhood of 200° C.; and the entire reaction can be conducted at approximately the melting point of the copolymer. Operation at the lower temperatures decreases the rate of degradation of the polymer which gives a polymer of lighter color. Another advantage is that the copolymer can be successfully quenched when being extruded into film because the copolymer is less crystalline. On the other hand, the homopolymer shows a greater tendency to crystallize on extrusion and thereby tends to form opaque areas in the film.

Example 4 of said U.S. Pat. No. 2,668,162 shows reaction conditions.

Surgical elements of polyglycolic acid, including sutures, and other elements mentioned below can be better seen in most surgical fields if the element is colored so as to contrast with blood and tissue or bandages or other background materials. It is desirable that such elements be colored during manufacture with a dye or pigment which has no surgical disadvantages of its own, and which either has no effects on the polymer or improves its characteristics.

Colorants such as iron oxide or carbon black have been used to color non-absorbable sutures of polymers such as nylon or linear polyethylene or isotactic polypropylene. As such polymers are not absorbed, the colorant is removed when the suture is removed so completely non-absorbable pigments are satisfactory.

With an absorbable suture, as the suture is absorbed, the colorant is released into the living mammalian tissue, and its toxicity and metabolic fate become a matter of concern. It is necessary that any color component be tissue compatible. Usually, it is desirable that the colorant disappear to avoid tattoo traces in the tissue after the wound heals and the suture is absorbed.

BRIEF DESCRIPTION OF PRIOR ART

U.S. Pat. No. 3,297,033, Schmitt & Polistina, SURGICAL SUTURE, Jan. 10, 1967 describes polyglycolic acid sutures and in Column 3, line 48 mentions the incorporation of dyes and the sentence bridging Column 3 and 4 discloses green or blue sutures so that the suture will stand out against fields of contrasting colors.

British patent 988,939, Voss and Joachim describe in Example 3 the polymerization of glycolide with coloring agents such as a mixture of titanium dioxide and Indanthrene Brillant Green B. [K. Venkataraman, Synthetic Dyes, 1952 gives the structure as:

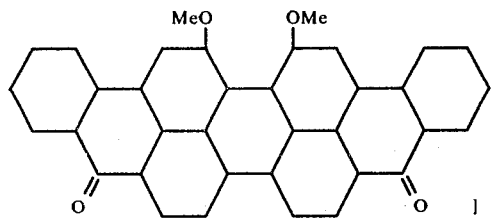

Canadian patent 863,673, Feb. 16, 1971, A. K. Schneider on page 22 describes polyactide sutures containing the monosodium salt of 4-[4-(N-ethyl-p-sulfobenzylamino)diphenylmethylene]-[1-(N-ethyl-N-p-sulfoniumbenzyl)-$\Delta^{2,5}$-cyclohexadienimine]. (FD&C Green No. 1) [The Colour Index, second edition 1956, and Merck Index 1968, shows FD&C Green No. 1 to be a positional isomer of the above recited formula with a structure:

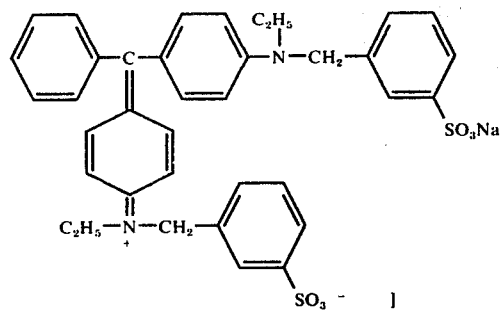

(Venkataraman shows para sulfo groups, page 714)

U.S. Pat. No. 3,636,956, Jan. 25, 1972, A. K. Schneider in Example XVI has a similar disclosure.

The coloring of sutures in general is quite old with isotactic polypropylene and linear polyethylene sutures being colored green or blue; and with many silk sutures being dyed black, and other colors being selected for identification of the ends of different sutures in preplaced sutures. Identification can be made of suture types or characteristics with either inherent or selected colors used as a code system. Color is used to make the suture contrast better with the blood or tissue in an operating area, or with dressings or bandages, when visibility is to be enhanced.

Surgical sutures and other surgical elements of polyglycolic acid are described in:

U.S. Pat. No. 3,297,033, Jan. 10, 1967, Schmitt and Polistina, SURGICAL SUTURES.

U.S. Pat. No. 3,463,158, Aug. 26, 1969, Schmitt and Polistina, POLYGLYCOLIC ACID PROSTHETIC DEVICES. Reference is made to these patents which show additional prior art and for the definitions therein set forth.

Related data incorporated herein by this reference on manufacturing of polyglycolic acid, producing surgical elements thereof and its use for surgical purposes are disclosed in:

U.S. Pat. No. 3,414,939 — December 10, 1968, Chirgwin, APPARATUS FOR QUENCHING MELT-SPUN FIBERS.

U.S. Pat. No. 3,422,181 — Jan. 14, 1969, Chirgwin, METHOD FOR HEAT SETTING OF STRETCH ORIENTED POLYGLYCOLIC ACID FILAMENT.

U.S. Pat. No. 3,435,008 — Mar. 25, 1969, Schmitt, Epstein and Polistina, METHOD FOR PREPARATION OF ISOMERICALLY PURE $\beta$-GLYCOLIDE AND POLYMERIZATION METHOD FOR GLYCOLIDE COMPOSITIONS EMPLOYING PARTIAL HYDROLYZATE OF SAID $\beta$-GLYCOLIDE.

U.S. Pat. No. 3,442,871 — May 6, 1969, Schmitt, Epstein and Polistina, PROCESS FOR POLYMERIZING A GLYCOLIDE.

U.S. Pat. No. 3,457,280 — July 22, 1969, Schmitt, Epstein and Polistina, $\alpha$-GLYCOLIDE AND METHODS FOR THE ISOLATION THEREOF.

U.S. Pat. No. 3,468,853 — Sept. 23, 1969, Schmitt and Polistina, PROCESS OF POLYMERIZING A GLYCOLIDE.

U.S. Pat. No. 3,565,077 — Feb. 23, 1971, Glick, DENSIFIED ABSORBABLE POLYGLYCOLIC ACID SUTURE BRAID, AND METHOD FOR PREPARING SAME.

U.S. Pat. No. 3,565,869 — Feb. 23, 1971, DeProspero, EXTRUDABLE AND STRETCHABLE POLYGLYCOLIC ACID AND PROCESS FOR PREPARING SAME.

U.S. Pat. No. 3,597,449, Aug. 3, 1971, DeProspero and Schmitt, STABLE GLYCOLIDE AND LACTIDE COMPOSITIONS.

U.S. Pat. No. 3,597,450, Aug. 3, 1971, Schmitt, Polistina, Epstein and DeProspero, PREPARATION OF GLYCOLIDE POLYMERIZABLE INTO POLYGLYCOLIC ACID OF CONSISTENTLY HIGH MOLECULAR WEIGHT.

U.S. Pat. No. 3,600,223, Aug. 17, 1971, Glick and McCusker, PROCESS FOR CLEANING POLYGLYCOLIC ACID FILAMENTS USEFUL AS ABSORBABLE SURGICAL SUTURES.

U.S. Pat. No. 3,620,218, Nov. 16, 1971, Schmitt and Polistina, CYLINDRICAL PROSTHETIC DEVICES OF POLYGLYCOLIC ACID.

U.S. Pat. No. 3,626,948, Dec. 14, 1971, Glick and McPherson, ABSORBABLE POLYGLYCOLIC ACID SUTURE OF ENHANCED IN-VIVO STRENGTH RETENTION.

U.S. Ser. No. 34,593, May 4, 1970, Schmitt and Bailey, SOLUTIONS OF POLYGLYCOLIC ACID, now abandoned in favor of an application issuing as 3,737,440, June 6, 1973.

U.S. Ser. No. 117,998, Feb. 23, 1971, Semp, STERILE SURGICAL GLOVES, now U.S. Pat. No. 3,728,739, Apr. 24, 1973.

U.S. Ser. No. 118,974, Feb. 25, 1971, Ramsey and Delapp, PREPARATION OF POLYGLYCOLIC ACID IN FINELY DIVIDED FORM, now U.S. Pat. 3,781,349, Dec. 25, 1973.

U.S. Ser. No. 138,425, Apr. 29, 1971, Glick, STORAGE STABLE SURGICALLY ABSORBABLE POLYGLYCOLIC ACID PRODUCTS, now U.S. Pat. 3,728,839, Apr. 24, 1973.

U.S. Ser. No. 157,521, June 28, 1971, Schmitt and Polistina, POLYGLYCOLIC ACID PROSTHETIC DEVICES, now U.S. Pat. 3,739,773, June 19, 1973.

SUMMARY OF THE INVENTION

It has now been found that polyglycolic surgical elements may be colored with 1,4-bis(p-toluidino)anthraquinone. This material has the formula:

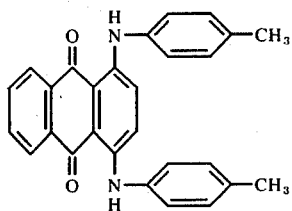

it is sometimes known as D&C Green No. 6 when in drug grade and is also identified as Solvent Green 3 and bears Colour Index No. 61565.

This invention relates to a method for the formation of green colored polyglycolic acid for use as non-tattooing surgical elements, and the surgical elements thereunder, including sutures comprising the steps of:

a. mixing and heating 1,4-bis(p-toluidino) anthraquinone with polyglycolic acid b. to form a solution of 1,4-bis(p-(toluidino) anthraquinone uniformly dispersed in polyglycolic acid by c. mixing 1,4-bis(p-toluidino)anthraquinone and polyglycolic acid and heating to form a solution d. cooling the solution to form a solid solution of green colored polyglycolic acid, including e. either using the thus formed green colored polyglycolic acid as such, or f. forming a "masterbatch" in which the 1,4-bis(p-toluidino)anthraquinone is dissolved at a concentration of from about 1% to about 10%, and diluting the concentrated masterbatch either g. as a solution with additional polyglycolic acid or h. a cooled dry solid, with i. additional polyglycolic acid to form a mixture of the desired 1,4-bis(p-toluidino)anthraquinone concentration by j. admixing the solid solution of green colored polyglycolic acid with dry solid polyglycolic acid;

k. heating the resulting mixture to form a solution of 1,4-bis(p-toluidino)anthraquinone in polyglycolic acid; and l. cooling the solution formed to produce a solid solution of green colored polyglycolic acid having a reduced concentration of about 0.03% to 0.5% by weight of 1,4-bis(p-toluidino)anthraquinone in polyglycolic acid;

m. and fabricating a surgical element therefrom.

It is found that 1,4-bis(p-toluidino)-anthraquinone when used to color a surgical element such as a suture is tissue compatible and introduces no complications in healing.

Additionally 1,4-bis(p-toluidino)-anthraquinone is non-tattooing.

If sutures are used near the surface of the skin, and coloration is used in the suture, the residual coloring matter may be left in the tissue so that it is visible through the skin as a tattoo. Such materials as carbon black and iron oxides if used as a pigment in an absorbable suture may remain in the tissue indefinitely, leaving a permanent mark. In experimental animals it may be desirable that a tattooing colorant be used in order that the location of the suture can be traced by the residual color even if the suture has been absorbed. Although there may be surgical procedures in which it is desirable that tattoo marking remain, for the vast majority of surgical uses it is desirable that the colorant used in the suture or other surgical elements be absorbed by the living tissue or otherwise removed as the polyglycolic acid is absorbed.

1,4-bis(p-toluidino)-anthraquinone absorbs readily, it is tissue compatible, and it causes no complications during the healing process. Additionally it is non-tattooing, so that as the suture is absorbed, the color disappears.

The same advantages of identifiability during use and absorption of color later by tissues are found in other surgical elements of polyglycolic acid (PGA).

The PGA may be formed as tubes or sheets for surgical repair and may also be spun as thin filaments and woven or felted to form absorbable sponges or absorbable gauze, or used in conjunction with other compressive structures as prosthetic devices within the body of a human or animal where it is desirable that the structure have short-term strength, but be absorbable. The useful embodiments include tubes, including branched tubes or Tees, for artery, vein or intestinal repair, nerve splicing, tendon splicing, sheets for tying up and supporting damaged kidney, liver and other intestinal organs, protecting damaged surface areas such as abrasions, particularly major abrasions, or areas where the skin and underlying tissues are damaged or surgically removed.

In surgical techniques involving internal organs, hemorrhage may be a major problem. Some of the organs have such tissue characteristics that it is very difficult to use sutures or ligatures to prevent bleeding. For example, the human liver may suffer traumatic damage or exhibit tumors or for other reasons require surgery. In the past it has been very difficult to excise part of the liver or to suture the liver without the combined problems of the sutures cutting out and hemorrhage at the surface causing such major complications as to either prevent surgery or cause an unfavorable prognosis.

It is now found that a sponge or pad or velour of polyglycolic acid may be used to protect the surface and permit new feats of surgical intervention. For instance polyglycolic acid filaments may be formed into a woven gauze or felted sponge of a velour, preferably the construction is fairly tight by textile standards, and such sponge may be placed on the surface of the bleeding organ such as the liver or a lung with either gentle suturing to hold the element or with ties in the nature of ligatures to hold the element in position with a certain amount of body fluids flowing into the sponge and being absorbed, which results in hemostasis and prevention of further loss of body fluids. If a liver or lung is so repaired, the organ may be replaced in the body cavity and the wound closed. Note the technique in Didusch 2,143,910. The polyglycolic acid elements usually maintain a substantial portion of their strength for at least 7 to 15 days which permits healing processes to occur and then the polyglycolic acid is absorbed by the body so that in healthy living tissue with good blood supply, the prosthetic device is completely absorbed in 60 to 90 days.

When colored green, these surgical elements are more easily seen by the surgeon, and hence are easier to place and control during surgery. Additionally, the location of partially absorbed polyglycolic acid is more readily ascertained in experimental animals on sacrifice, or an autopsy should a patient fail to survive.

Pads, bandages or sponges of polyglycolic acid are extremely useful in surgical techniques in which it is the intent to remove the major portion or all of such sponges, felt or pad but through inadvertence or accident part of it may remain. For instance in a surgical operation, one of the problems which arises is the lint from cotton sponges remaining in the wound. If polyglycolic acid sponges are used, any small fragments which are accidently displaced are absorbed without incident and even if a sponge is left in the wound, the deleterious effects are minimal.

The green color aids in locating sponges by inspection before the wound is closed.

The use of polyglycolic acid as a sponge or pad is particularly advantageous for surface abrasions. In the past it has been necessary to put on a dressing and avoid having the non-absorbable dressing grow into the the tissue at all costs. Because the polyglycolic acid absorbs, if elements of polyglycolic acid gauze are beneath the regenerating tissue level, the tissue will regenerate and absorb polyglycolic acid with the residual polyglycolic acid in the scab falling off when the scab is displaced, without tattooing.

Even in cosmetic surgery or skin surgery, where in the past it has been quite customary to use silk sutures and, after the tissue is regenerated sufficiently to be self retaining, remove the sutures so that they do not leave scars, the use of polyglycolic acid sutures now permits implantation of sutures through the skin with the part below the skin surface being absorbed and the part above the skin surface falling off when it is no longer retained by the polyglycolic acid below the skin. The resulting minimal degree of scarring at the skin surface is highly advantageous.

The green color lasts long enough to permit inspection of suture location during the earlier and middle phases of healing.

In surgery various tissues need to be retained in position during healing. Defects and wounds of the abdominal wall, chest wall and other such tissues need to be reconstructed. For a hernia, a permanent splice or reinforcement is often desired. For some surgical procedures, a temporary reinforcing is desired to provide strength while body tissues are healing; and after the body tissues have assumed the load, foreign components are no longer desired. Tissue retention is readily accomplished using either an absorbable PGA monofilament or polyfilament fabric or mesh or by using a non-absorbable material such as polyethylene or polypropylene or polyester woven as a bicomponent mesh or knit with PGA. The use of a bicomponent fabric has the advantage of giving additional early strength for holding the tissues in position during initial regeneration with the PGA portions being absorbed, and permitting body tissues to invade and reinforce the permanent mesh.

In common with other surgical procedures, it is often desirable that a bicomponent structure be used which provides the spacing desired for non-absorbable elements, with the PGA element holding the structure in a desired geometrical configuration at the start of the healing process. As the polyglycolic acid element is absorbed, regenerated tissue invades and replaces the dissolved PGA so that the non-absorbed element is left in a desired configuration, interlaced with living tissue in a stress-transferring relationship.

The choice of a non-absorbable reinforcement, a partially absorbable reinforcement, or a completely absorbable reinforcement is a matter of surgical judgment, based upon the condition of the patient, the body structure under treatment, and other medical factors. The present PGA fabric, or bicomponent fabrics using PGA for the absorbable portion greatly expand the scope of reinforcement available to a surgeon, and permits using absorbable structures for reinforcement in many new medical techniques.

If the polyglycolic acid is colored green, and the permanent reinforcing elements are colorless or white, the surgeon is more rapidly able to ascertain which elements are permanent.

For instance, a PGA sponge may be used in a cavity after tooth extraction to stanch the flow of blood. The sponge is either absorbed by regenerating tissue, or disintegrates into the mouth, permitting improved recovery after extractions.

The PGA may be exposed to moisture during storage before use, or may be of a lower molecular weight, both of which increase the rate of absorption by the body tissues, so that the surgical sponge in an extraction, or the prosthetic implant, has a controllable rate of absorption.

The surgical elements of green polyglycolic acid include, but are not necessarily limited to:

A. Single Component PGA Products
 1. Solid Products, molded or machined
   a. Orthopedic pins, clamps, screws and plates
   b. Clips (e.g., for vena cava)
   c. Staples
   d. Hooks, buttons and snaps
   e. Bone substitue (e.g., mandible prosthesis)
   f. Needles
   g. Non-permanent intrauterine devices (spermicide)
   h. Temporary draining or testing tubes of capillaries
   i. Surgical instruments
   j. Vascular implants or supports
   k. Vertebral discs
   l. Extracorporeal tubing for kidney and heart-lung machines
 2. Fibrillar Products, knitted or woven, including velours
   a. Burn dressings
   b. Hernia patches
   c. Absorbent paper or swabs
   d. Medicated dressings
   e. Facial substitutes
   f. Gauze, fabric, sheet, felt or sponge for liver hemostasis
   g. Gauze bandages
   h. Dental packs
   i. sutures, including ligatures
 3. Miscellaneous
   a. Flake or powder for burns or abrasions
   b. Foam as absorbable prosthesis
   c. Substitute for wire in fixations
   d. Film spray for prosthetic devices
B. PGA in Combination with other Products
 1. Solid Products, molded or machined
   a. Slowly digestible ion-exchange resin
   b. Slowly digestible drug release device (pill, pellet)
   c. Reinforced bone pins, needles, etc.
 2. Fibrillar Products
   a. Arterial graft or substitutes
   b. Bandages for skin surfaces
   c. Burn dressings (in combination with other polymeric films.)

It is also found that the mixture of polyglycolic acid and 1,4-bis(p-toluidino)-anthraquinone is optically homogeneous. By this is meant that when observed under an optical microscope, at the limits of resolution of an optical microscope, the polyglycolic acid of the suture appears as a clear green glass, with the green coloration being uniformly distributed throughout and without particulate 1,4-bis(p-toluidino)-anthraquinone being visible. The mixture appears to be a solid solution, having a single homogeneous phase.

Solubilities of chemical compounds are among the more predictable qualities.

Even among related compounds anomalies in solubilities are common. Here for example, polyglycolic acid is insoluble in all common organic solvents. It is soluble enough for viscosity measurements to determine molecular weights in exotic solvents such as hexafluoroisopropyl alcohol and hexafluoroacetone sesquihydrate. The adjacent homologue polylactic acid is soluble in common benzenoid solvents, such as benzene, toluene or xylene (see Canada 863,673 supra).

Hence any conjectures of solubility in or of polyglycolic acid from studies of other related compounds would be speculative.

Pigments which are insoluble particles would be visible in an optical microscope and would be much more apt to leave residual traces in tissue.

Polyglycolic acid does not appear to be dyed by ordinary dyes. A dye, to be useful, must be substantive to the substrate, that is be absorbed on and remain with the substrate without being readily removed therefrom during washing or other procedures. Many dyes are substantive to one material and not another and would hence not be absorbed at all or would be readily washed off the surface. Pigments would be much more apt to show color strength but would not be homogeneous, and might remain as discrete particles in the healed tissue.

Fortunately and fortuitously and most unexpectedly 1,4-bis(p-toluidino)-anthraquinone also improves the spinning characteristics of polyglycolic acid under many conditions.

The theoretical aspects are at best subject to postulation. It may be that a small proportion of 1,4-bis(p-toluidino)-anthraquinone adheres to the exterior surface of the polyglycolic acid particles and aids in feeding them through a screw extruder or it may be that it is a melting on the surface that acts as a lubricant.

It is found that under some conditions when the extrusion does not run smoothly otherwise, the incorporation of 1,4-bis(p-toluidino)-anthraquinone will increase the extrudability and increase the homogeneity of the extruded product. Additionally, the colored polyglycolic acid filaments when extruded stretch more uniformly.

Important in the extrudability is the fact that 1,4-bis(p-toluidino)-anthraquinone melts at about 225° C. which is very close to the melting point of polyglycolic acid and accordingly, the components mix as completely miscible liquids to form a homogeneous colored liquid which is extruded, and as extruded and melt spun to form a fiber, the two components solidify as a solid solution rather than as dispersed pigment particles in a continuous phase.

This may in part account for the high color value of the 1,4-bis(p-toluidino)-anthraquinone in the polyglycolic acid, and also may in part account for improved stretchability. It may be that small quantities of the 1,4-bis(p-toluidino)-anthraquinone prevent premature crystallization and hence permit the strand to be spun before it crystallizes and cause the strand to crystallize more uniformly. Polyglycolic acid alone may be melt spun to give an extremely satisfactory solid surgical element such as a suture. The incorporation of 1,4-bis(p-toluidino)-anthraquinone increases the ease of spinning under some conditions. The purpose of the present application is to explain the practical not the theoretical aspects and hence the present invention is not predicated upon any theoretical explanation of the interaction between the 1,4-bis(p-toluidino)-anthraquinone and the polyglycolic acid.

The fact that the introduction of 1,4-bis(p-toluidino)-anthraquinone improves the extrudability is a most unexpected advantage and attribute.

The feel and handling characteristics of sutures are very important, but difficult to define. Some surgeons report that the green colored sutures have improved handleability and superior knot tying characteristics, and the knots hold better.

EXAMPLE 1

To confirm the ready solubility of 1,4-bis(p-toluidino)-anthraquinone in polyglycolic acid, some short pieces of polyglycolic acid sutures were melted and thereto added a small amount of 1,4-bis(p-toluidino)-anthraquinone. It dissolved therein and colored the polymer uniformly. On spinning, the green colored polyglycolic acid appeared to be satisfactory as a suture. The quantity of 1,4-bis(p-toluidino)-anthraquine added can vary widely. If less than about 0.03% is present, the coloration imparted to the polyglycolic acid is lower than preferred for most surgical uses. If more than about 0.4% is added, the depth of color is unnecessarily increased without commensurate advantages. 0.3% colors the polymer so that it stands out extremely well under any conditions where color is required and additional coloration is not necessary for normal uses.

A far higher degree of coloration may be introduced in processing. For instance 1% to 5% of 1,4-bis(p-toluidino)-anthraquinone may be melted with polyglycolic acid to form a masterbatch. The color is readily uniformly dispersed throughout the polymer with a minimum of mixing being required and the polymer is extruded or otherwise subdivided as for instance by breaking into chunks or grinding, with the heavily colored polymer to be added to uncolored polymer to reduce blending requirements for even coloration. The use of a masterbatch containing a large proportion of coloring agent is frequently used in the production of filamentary materials. It is often convenient to incorporate the coloring agent at a higher concentration in a portion of the polymer, with the highly colored polymer later diluted for use. This permits the more uniform incorporation of the colorant with less mixing than would putting a small proportion of the color into all of the polymer and mixing to blend. This is frequently referred to as a masterbatch operation.

Standard techniques for polymerization to form polyglycolic acid, its spinning, braiding and processing into sutures are compatible with the use of 1,4-bis(p-toluidino)-anthraquinone as a coloring material. Hence any of the processes above described in the prior art including copending patents and applications represent independent processing inventions which may be used on green colored polyglycolic acid. The extrusion characteristics are improved so that less power and lower torque on the extrusion equipment may be used, or higher production rates are achieved.

Similar results are obtained when small quantities, i.e., up to 15%, of lactic acid are copolymerized in the polyglycolic acid. The melting point, and hence the extrusion temperature is lowered, slightly, but effectively a small quantity of lactic acid does not change the characteristics and the material is considered polyglycolic acid. The term homopolymer or pure polyglycolic acid can be used to distinguish polymers in which immaterial quantities of other components are absent.

The dispersion of the color through a polymer, or precursor, before it is spun into a fiber is normally referred to in the trade as "dope dyeing" from the days when dopes were used as a spinning medium. The term "dope" was frequently used to refer to a solvent solution of a material being spun. The solvent solution was colored, the dope spun, the solvent was stripped off, with the spun fiber retaining the coloring matter uniformly dispersed throughout its cross-section, as contrasted with dyed or surface colored materials in which the dye or surface coloration is added to the surface of the fibers after they are formed. Tests on the fibers so prepared showed that the 1,4-bis(p-toluidino)-anthraquinone did not "bleed" into surrounding tissues and that the tissue reaction was normal in all instances. In due course after the polyglycolic acid had been absorbed, the green was also absorbed leaving the tissues without stain or tattooing On implantation in test animals, the colored suture was easier to see during placement and appeared to absorb uneventfully in the tissue with the same characteristics as uncolored polyglycolic acid prepared and spun under otherwise similar conditions. During early stages of healing, the green 1,4-bis(p-toluidino)-anthraquinone could be seen in the suture and the suture was more readily located in tissue because of its color but as the suture absorbed, the 1,4-bis(p-toluidino)-anthraquinone was released into the tissue and was absorbed.

After 90 days, both colored and non-colored suture had been absorbed and no residual 1,4-bis(p-toluidino)-anthraquinone was observable.

In other tests, the green 1,4-bis (p-toluidino)-anthraquinone was observable in tissue after the polyglycolic acid had appeared to have been absorbed, and sometimes could be observed in interrupted tracts at 90 days although the green completely disappeared shortly thereafter. Because the green makes the sutures stand out more clearly in the tissue, at casual or close inspection, the colored sutures are much easier to find even though the actual absorption is effectively the same as the uncolored sutures, so that coloration can disappear more slowly than the apparent disappearance of uncolored sutures. In no instances does tattooing or coloration remain in healthy living tissue for an objectionably long time.

In similar tests samples were prepared by polymerizing glycolide having present (A) 4.5 mole % lactide, (B) 12 mole % lactide, and (C) 22 mole % lactide. A chloroform solution containing 0.5% w/v of 1,4-bis(p-toluidino)anthraquinone was added so that a total of 0.5% by weight of 1,4-bis(p-toluidino)anthraquinone was added to portions of the polymers. The solvent was flashed off, and as the polymer softened, the 1,4-bis(p-toluidino)-anthraquinone dye dissolved in the melting polymer. A homogeneous melt resulted, from which fibers were drawn by contact and drawing out a glass rod. Samples were drawn as fibers at (A) 210° C. (B) 180°–185° C. and (C) 185°–190° C. The homogenity of the fibers drawn under a microscope showed the dye had dissolved.

Extrusion techniques as elsewhere described give good results in larger batches. The slightly lower melting point of polyglycolic acid containing up to 15% lactic acid and the preparation of such polyglycolic acid is described in U.S. Pat. No. 2,668,162 supra.

EXAMPLE 2

Colored fibers were prepared by spinning mixtures of each of 1,4-bis(p-toluidino)-anthraquinone, a red iron oxide pigment and a carbon black pigment with separate portions of fines screened from the grinding of polyglycolic acid preparatory to melt spinning. The 1,4-bis(p-toluidino)-anthraquinone, the iron oxide and the carbon black were each added in the proportion of 0.5 parts of color to 100 parts of polymer and dispersed by tumbling in a ball mill. For comparative purposes, an extrusion machine was set up to melt spin uncolored polyglycolic acid with the production of filaments which were later stretched around godets. The mixed polymer containing the 1,4-bis(p-toluidino)-anthraquinone was charged to the spinning equipment and was spun uneventfully. The samples containing the iron oxide and the carbon black were each charged in turn. Shortly after the charging of the polymer containing the carbon black, the equipment plugged up apparently from the deposition of iron oxide in the filter which was used to keep solid particles from clogging the spinning jets.

EXAMPLE 3

Following the procedure of U.S. No. 3,442,871, supra, as there set forth in Examples A and 1,: Into a suitable reaction vessel there is charged 400 parts of a commercial glycolic acid which is then heated from room temperature to about 200° C. over a period of about 4 hours. When the pot temperature has reached 185° C., the pressure of the system is reduced from atmospheric pressure to 15 mm. of Hg. causing the water of condensation and/or esterification to distill off. The residue is allowed to cool and is pulverized into about 280 parts of a powder which is then added in small increments to a suitable pyrolysis chamber maintained at a temperature of about 250°–285° C. at a pressure of less than 15 mm. of Hg. The distillate which weighs about 238 parts is dissolved in a minimum amount of hot ethyl acetate, and after decolorizing and purifying with active carbon, the distillate is recrystallized from the above solution to provide 160 parts of product having a melting point of about 82.5°–84.0° C. The infrared spectrum confirms that the product is substantially identical to substantially pure of glycolide composition.

Into a heavy walled glass tube having a bore about 3/10 inch and sealed at one end is charged about 3 parts of substantially pure glycolide composition produced as above, 0.04 part of a 0.1% ether solution of $SnCl_2 \cdot 2H_2O$ (about 0.0013% of $$SnCl_2 \cdot 2H_2O$$

based on the weight of the substantially pure glycolide composition), 0.0166 part of lauryl alcohol (0.346 mole percent based on the moles of the substantially pure glycolide composition), and a magnetic steel ball 5/32 inch in diameter. The tube is evacuated and purged with argon. The tube is evacuated again to a vacuum of less than 1 mm. of Hg and the top is sealed. The reaction tube is placed in a vertical position in a closed glass chamber throughout which dimethyl phthalate is refluxed at 222° C. The boiling point of the dimethyl phthalate is controlled by decreasing the pressure of the system. At periodic intervals after melting, the viscosity of the reaction mixture is measured by raising the steel ball by means of a magnet and measuring the rate of the fall of the ball in sec./in. Ninety minutes after the melt is first achieved, the ball drop time is 550 sec./in. or about 7,200 poises, and after 120 minutes, the ball drop time is 580 sec./in. or about 7,600 poises.

The thus formed polymer, while maintaining protection from ambient moisture, is cooled, ground to a coarse mesh and is then ready for melt spinning.

EXAMPLE 4

100 parts of polymer prepared as above is ground with 1 part of 1,4-bis(p-toluidino)-anthraquinone, the polymer melted, stirred until homogeneous and again cooled and ground. This dried polymer containing 1% of 1,4-bis(p-toluidino)-anthraquinone is mixed with 10 times its quantity of uncolored polyglycolic acid, placed in a melt spin extruder, filtered, and forced through spinning apertures under high pressure, in accordance with conventional melt spinning techniques.

When finished and braided into a surgical suture, an excellent green colored suture is obtained.

EXAMPLE 5

To pellets of freshly prepared polyglycolic acid was added 0.1% 1,4-bis(p-toluidino)anthraquinone as a powder, and shaken to mix. The mixture was introduced into a melting tube, melted, and spun through a spinnerette having a diameter of about 1.5 mils in accordance with the procedures set up in U.S. Pat. No. 3,422,181 supra. The finished filament appeared to have characteristics the same as the uncolored filaments except for the color. The filaments were processed into sutures using the same techniques as with the uncolored suture and a beautiful green suture resulted.

Part of the filament produced was subjected to heat treatment to volatilize impurities in accordance with U.S. Pat. No. 3,626,948 supra.

While volatilizing the impurities, part of the 1,4-bis(p-toluidino)anthraquinone is also volatilized. There is a tendency for the green color to migrate to and concentrate on the surface. Wiping the surface with a sponge or felt saturated with xylene, or washing in xylene removes the surface color, and reduces the tendency to "crock" or rub off on the surgeons gloves, or other materials which may contact the suture. Because of the intense color, the rub off looks very noticable, even if only a small amount actually rubs off. During the heat treatment and washing, minor quantities of the green color may be lost. A slightly higher feed rate can compensate for such loss, and the feed rate of green is best adjusted to give a desired intensity of color. In volatilization, care must be used to prevent green color being transferred to subsequent batches of clear polymer, if the same equipment is used.

The green colored filament was as readily processed into sutures as the uncolored filament and turned out to have properties at least as good as the uncolored polyglycolic acid.

It thus appears that the presence of the small amount of 1,4-bis(p-toluidino)-anthraquinone required to give a desirable green color to the surgical elements, particularly sutures, permits processing, including spinning and braiding and usages for the same purpose as uncolored polyglycolic acid. The green colored material is more readily observed in a surgical field.

EXAMPLE 6

A substantial quantity of polyglycolic acid prepared in pilot plant equipment following the procedure of U.S. Pat. No. 3,442,871, and as described in Example 3 was subjected to vacuum stripping, commonly known as a finishing treatment, as described in U.S. Pat. No. 3,565,869 supra. This includes heating the ground or pelletized polyglycolic acid to about 165° C. under a reduced pressure of 40 mm. Hg. or less while passing hot, dry, oxygen-free inert gas over or through the polymer bed to essentially eliminate or substantially reduce any residual glycolide, moisture, or other relatively volatile impurities.

Approximately equal quantities of about one pound each of the "finished" polymer were placed in each of four separate containers of comparative melt spinning tests. One sample was used for reference. The others were dry-blended with colorants by adding 0.2% Ferro-Blue 0.4% 1,4-bis(p-toluidino)-anthraquinone and 0.2% Carbon Black, respectively, the colorants having been vacuum dried at 110° C. overnight under 5 mm. Hg. pressure. The containers were sealed immediately and thoroughly shaken to disperse the colorants among the polyglycolic acid particles.

The four variants were then melt spun sequentially at 235° C., through a ¾ inch Brabender melt extruder having a length to diameter ratio of 25 to 1, and fitted with a heated spinning head which carried a metering pump, filter, and spinneret.

In melt spinning it is desirable to maintain a high level of metering efficiency through the melt pump. This is achieved by delivering the polymer melt from the extruder to the pump at approximately the same pressure which the pump generates in forcing the molten polymer through the spin pack. Thus the pump drive is relieved of a substantial load, insuring minimal deviation from the desired pumping rate. Also, no pressure differential exists to oppose the advance of the molten polymer through the pump, so the metering action is more precise.

Polyglycolic acid is a very hard and tough polymer, demanding torques close to the limit of the Brabender extruder used in these tests under effective conditions of extrusion. To avoid overloading the extruder drive, the screw speed must be kept low, resulting in low throughput, which necessitates a low pump speed also, to avoid a starved condition at the pump inlet. Extrusion conditions were established on the natural or uncolored reference polymer, and changes in machine response and product characteristics were observed on the sequentially extruded colored samples.

High and erratic torque limited the extruder screw speed to 7 rpm on the natural polymer. By adjusting pump speed to 15.5 rpm a balanced pressure of about 1,800 psi into and out of the pump was maintained.

When the Ferro Blue colored polymer entered the machine, the torque increase threatened to overload the drive, so screw speed was cut about 30% to 5 rpm, which generated an erratic extruder pressure of 1200 to 1800 psi, as pump pressure decreased to about 1500 psi.

The polymer carrying the 1,4-bis(p-toluidino)-anthraquinone, however, produced a gross reduction of torque so that the screw speed could be raised 1,100% to 60 rpm, (or higher if desired), which was required to raise the extruder pressure to match the pump output pressure of 1,500 psi. In addition to the gross reduction in torque, the large, erratic variations in both torque and extruder pressure moderated, and the operation ran smoothly and easily, suggesting a plasticizing or lubricating effect from using 1,4-bis(p-toluidino)-anthraquinone as the colorant.

The polymer containing the carbon black caused such a large torque increase, however, in spite of prior reduction in machine speed to about 20 rpm, that power could not be reduced in time to avoid breaking the shear pin in the extruder drive. Rather than acting as a lubricant, this colorant acted as a filler.

Visually, the green filaments appeared more deeply colored than necessary for use as sutures, while the blue and black filaments were too pale in hue to be acceptable.

Microscopic examination at 400X magnification revealed a uniform color dispersion in the green filaments, much like colored glass, and characteristic of a true solution. On the other hand, the individual pigment particles were observed to be widely scattered throughout the blue and black filaments, with very large, irregular, aggregates of varying size in the latter suggesting severe agglomeration.

EXAMPLE 7

Similar process responses were observed in other comparative spinnings. In particular, an extended run in which natural, uncolored, polymer was compared to identical material mixed with 0.1% 1,4-bis(p-toluidino)-anthraquinone yielded quantitative confirming data illustrating the benefits cited. In this test, extrusion conditions were again established and stabilized on the natural material, and about 30,000 feet of undrawn 16-filament yarn were collected over a period of 55 minutes, designated A in the table below.

Machine settings were left untouched as the natural material was followed by polymer containing 0.1% 1,4-bis(p-toluidino)-anthraquinone. As shown under sample C in the table, torque dropped to less than 25% of the preceding level and changed in nature from highly erratic to very stable. Pump pressure remained erratic, probably due to the reduced extruder pressure, but yarn properties were improved as indicated by the increased stretchability, and the physical properties of the drawn yarns. The term $TE^{1/2}$ is frequently used as an index of the toughness of a fiber and is calculated by multiplying the tensile strength, T, in grams per denier, times the square root of the percent elongation at the break.

The screw speed was then increased to take advantage of the low torque and to overfeed the pump to stabilize the pressure at the spinneret. It was found possible to more than double the screw speed; no other machine settings were changed; pump speed held constant at 21.4 rpm. This led to many benefits as shown under sample D, particularly in physical properties. About 18,000 feet of this undrawn material were collected in 30 minutes.

An excellent indication of undrawn yarn uniformity is a tensiometer reading taken on the yarn during stretching. Samples C and D demonstrate superior integrity and uniformity in this respect.

These results serve to illustrate the many advantages resulting from adding small quantities of 1,4-bis(p-toluidino)-anthraquinone to polyglycolic acid before melt spinning: (a) greatly reduced machine torque permitting (b) much higher screw speeds resulting in (c) far superior mastication and mixing, (d) more uniform melt both thermally and compositionally, and (e) potential for considerably increasing production; (f) more uniform undrawn yarn capable of developing (g) considerably improved physical properties possessing (h) excellent visibility under operating room conditions.

TABLE I

Effect of Addition of 1,4-bis(p-toluidino)-anthraquinone on Process Conditions and Quality of Polyglycolic Acid Melt Spun Yarns

| Test | A | C | D |
| --- | --- | --- | --- |
| % 1,4-bis(p-toluidino)-anthraquinone | None | 0.1 | 0.1 |
| Extruder Screw Speed, rpm | 12 | 14[a] | 32 |
| Extruder Torque, Meter-Grams | 7,400 (erratic) | 1,700 (steady) | 2,800 (steady) |
| Extruder Pressure, psi | 1,300 | 300 | 2,200 |
| Pump Pressure, psi | 2,130 (erratic) | 2,100 (erratic) | 1,950 (steady) |
| Undrawn Yarn Properties: | | | |
| Max. Stretch at 60° C.; 10 fpm | 2.7× | 2.9× | 3.8× |
| Stretch Tension, grams | 85 (erratic) | 115 (sl. erratic) | 195 (steady) |
| Drawn Yarn Properties: | | | |
| Tenacity, grams/denier | 3.6 | 4.2 | 6.3 |
| Elongation, % | 29 | 27 | 22 |
| Toughness Index, TE ½ | 19.4 | 21.8 | 29.1 |

[a]Speed control setting was unchanged from that for Test "A".

Although excellent sutures and other surgical elements are obtained with from 0.03% to 0.5% by weight of 1,4-bis(p-toluidino)-anthraquinone, a concentration of 0.1% to 0.2% by weight is preferred as giving a depth of color which is most acceptable to the medical profession.

We claim:

1. A method of coloring polyglycolic acid surgical elements comprising incorporating 1,4-bis(p-toluidino)-anthraquinone into molten polyglycolic acid to form an optically homogeneous solution and forming solid pellets therefrom, and later melt spinning the green colored polyglycolic acid pellets into filaments in which the 1,4-bis(p-toluidino)-anthraquinone is uniformly dispersed in an optically homogeneously solid solution, said 1,4-bis(p-toluidino)-anthraquinone providing both color and lubricity to aid in extension in the melt spinning.

2. The process of claim 1 in which the 1,4-bis(p-toluidino)-anthraquinone is uniformly dispersed in solid solution in homopolymeric polyglycolic acid at a concentration of about 0.03% to 0.5% by weight, and the extruded filaments are stretched and braided into a surgical suture.

3. The process of claim 2 in which the concentration of 1,4-bis(p-toluidino)-anthraquinone is between about 0.1% and 0.2% by weight.

4. The method of claim 1 in which the 1,4-bis(p-toluidino)-anthraquinone is incorporated into solid solution in polyglycolic acid at a greater concentration as a master-batch and then blended with uncolored polyglycolic acid and extruded to form a solid solution of 1,4-bis(p-toluidino)-anthraquinone in polyglycolic acid at a concentration of about 0.03% to 0.5% by weight.

5. The process of claim 4 in which the 1,4-bis-(p-toluidino)-anthraquinone is uniformly dispersed in solid solution in homopolymeric polyglycolic acid at a concentration of about 0.03% to 0.5% by weight, and the extruded filaments are stretched and braided into a surgical suture.

6. The process of claim 1 in which the 1,4-bis(p-toluidino)-anthraquinone is uniformly and intimately dispersed in solid solution in polyglycolic acid which has up to 15 mol percent of lactic acid linkages therein, and in which the 1,4-bis(p-toluidino)-anthraquinone is intimately dispersed in an optically homogeneous solid solution at a concentration of about 0.03% to 0.5% by weight, and the extruded filaments are stretched and braided into a uniformly colored green surgical suture.

7. The process of claim 4 in which the 1,4-bis(p-toluidino)-anthraquinone is uniformly and intimately dispersed in solid solution in polyglycolic acid which has up to 15 mol percent of lactic acid linkages therein, and in which the 1,4-bis(p-toluidino)-anthraquinone is intimately dispersed in an optically homogeneous solid solution at a concentration of about 0.03% to 0.5% by weight, and the extruded filaments are stretched and braided into a uniformly colored green surgical suture.

8. A method of coloring filamentary polyglycolic acid surgical elements comprising:
   intimately mixing dry 1,4-bis(p-toluidino)-anthraquinone and dry solid polyglycolic acid particles and melting to form an optically homogeneous solution, said 1,4-bis(p-toluidino)-anthraquinone and said polyglycolic acid melting and solidifying at about the same temperature,
   melt spinning the mixture through a spinnerette, solidifying the polyglycolic and 1,4-bis(p-toluidino)-anthraquinone concurrently to form a fiber, whereby the 1,4-bis(p-toluidino)-anthraquinone is uniformly dispersed in an optically homogeneous solid solution throughout the filamentary solid polyglycolic acid, and from which the 1,4-bis(p-toluidino)-anthraquinone is not leachable, and which on implantation and absorption by living mammalian tissue uniformly absorbs without tattooing,
   and subsequently stretching to orient,
   said 1,4-bis(p-toluidino)-anthraquinone providing both color and lubricity to aid in extrusion in the melt spinning.

9. A method of claim 8 in which the polyglycolic acid is homopolymeric and the 1,4-bis(p-toluidino)-anthraquinone is at a concentration of between about 0.03% to 0.5% by weight and the polyglycolic acid is extruded and stretched into oriented surgical filaments, and said filaments are braided into sutures.

* * * * *